United States Patent
Martin et al.

(10) Patent No.: US 7,212,110 B1
(45) Date of Patent: May 1, 2007

(54) IMPLANTABLE DEVICE AND SYSTEM AND METHOD FOR WIRELESS COMMUNICATION

(75) Inventors: Gregory R. Martin, Long Valley, NJ (US); Gregg Turi, Hackettstown, NJ (US); Marc Shanko, Newton, NJ (US); Rami Elghandour, Piscataway, NJ (US); Thomas Palma, Chester, NJ (US); William L. Winstrom, Andover, NJ (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 184 days.

(21) Appl. No.: 11/109,114

(22) Filed: Apr. 19, 2005

Related U.S. Application Data

(60) Provisional application No. 60/563,622, filed on Apr. 19, 2004.

(51) Int. Cl.
*G08B 1/08* (2006.01)
*A61N 1/00* (2006.01)

(52) U.S. Cl. .......................... 340/539.12; 340/825.69; 340/693.1; 340/333; 607/29; 607/33; 607/34; 607/61; 600/300; 128/903

(58) Field of Classification Search ........... 340/539.12; 607/29, 33
See application file for complete search history.

(56) References Cited

U.S. PATENT DOCUMENTS

| | | | | |
|---|---|---|---|---|
| 5,702,431 A | * | 12/1997 | Wang et al. | ................... 607/61 |
| 5,733,313 A | * | 3/1998 | Barrera et al. | ................ 607/33 |
| 5,814,089 A | * | 9/1998 | Stokes et al. | ................. 607/32 |
| 2004/0080299 A1 | * | 4/2004 | Forster et al. | .............. 320/114 |

* cited by examiner

*Primary Examiner*—Donnie L. Crosland
(74) *Attorney, Agent, or Firm*—Peter R. Lando; Christopher S. L. Crawford

(57) ABSTRACT

A wireless communication method and protocol, and wireless devices and systems for stimulation, are provided for communication between a wireless device and a charging device. During active wireless charging, communications (data transmission) from the wireless device to the charging device occurs via pulse loading the receive antenna of the receiving device. Because switching regulation in the receiving device may interfere with the communications, the switching regulation is disabled during a communications window. To further reduce the likelihood of misinterpretation of signals detected in the charging device resulting from the switching regulation or noise, the data bit rate of the pulse loading communications is maintained higher than the switching regulation frequency.

21 Claims, 3 Drawing Sheets

*FIG. 6A*  MESSAGE TABLE

| 3 CODES | MESSAGE |
|---|---|
| 1,4,8 | OVER - TEMPERATURE |
| 5,8,12 | OVER - CURRENT |
| 6,EOLH,EOLH+2 | CHARGING - END OF LIFE COUNTER HIGH NIBBLE |
| 7,EOLL,EOLL+6 | CHARGING - END OF LIFE COUNTER LOW NIBBLE |
| 8,11,15 | VOLTAGE LOW - HARDWARE DETECT |
| 11,14,2 | VOLTAGE LOW - SOFTWARE DETECT |
| 9,12,0 | CHARGING COMPLETE |
| 10,13,1 | VOLTAGE HIGH |

IMPLANTABLE DEVICE AND SYSTEM AND METHOD FOR WIRELESS COMMUNICATION

CROSS-REFERENCE TO RELATED APPLICATIONS

The present application claims priority to co-pending U.S. Provisional Patent Application No. 60/563,622, entitled "IMPLANTABLE DEVICE AND SYSTEM AND METHOD FOR WIRELESS COMMUNICATION," filed Apr. 19, 2004, the disclosure of which is hereby incorporated herein by reference.

TECHNICAL FIELD

The present invention relates to implantable medical devices, and in particular, to an implantable device and system and method for wireless communication for use in an implantable stimulation device.

BACKGROUND OF THE INVENTION

Prior art implantable devices have typically been powered by utilizing a permanent power source (e.g. battery) or by receiving power directly (e.g. wireless link) via an externally located device. Inclusion of a replenishable power sources (e.g. rechargeable battery) located within the implantable device is becoming commonplace. These power sources can be recharged during a recharging session via a direct electrical connection to an external device or via a wireless link. However, it is more practical to use a wireless link. Charging of the power source via wireless link typically occurs through the transmission and reception of an RF signal from the external device to the implantable device. One prior art system is that described in U.S. Pat. No. 6,381,496, which is incorporated herein by reference. Such charging sessions generally take from one to several hours to fully recharge the battery.

Typically, the implantable device includes another communications transceiver for communication with an external programming device. The external programming device functions to allow the patient or other person to program/control the operating characteristics of the implantable device. During the recharging session, the RF recharging energy is substantial and may interfere with the other communications between the implantable device and the external programming device. In addition, it is desirable to monitor the status of the charging operation and implantable device during the charging session. Errors or problems with the battery charging could pose significant safety issues and may require explanting of the device.

Accordingly, there is a need for an implantable device, external charging device, and wireless communication technique that will allow for communications from the implantable device during a recharging session and minimize any errors in such communications. Moreover, there is needed an implantable device, external charging device and communication technique that utilizes the wireless RF charging communications link as the means for communication.

BRIEF SUMMARY OF THE INVENTION

In accordance with one aspect of the present invention, there is provided a device for receiving wireless energy from a charging device. The device includes an antenna element operable for receiving wireless energy transmitted from the charging device. A switching regulator coupled to the antenna element includes circuitry for enabling operation of the switching regulator during a first predetermined time period and disabling operation of the switching regulator during a second predetermined time period. The enabling/disabling is in response to a switching regulator control signal and the switching regulator is operable for receiving and regulating the received wireless energy and outputting a regulated voltage. The device includes a pulse loading circuit coupled to the antenna element and operable for receiving one or more pulse loading pulses during the second predetermined time period. The one or more pulse loading pulses are operable for pulse loading the antenna element and the pulse loading of the antenna element is operable to transmit data to the charging device.

In accordance with another aspect of the present invention, there is provided a stimulation system for stimulating a portion of a body. The stimulation system includes the above-described device, and further includes an implantable lead for receiving a stimulus from the device and applying the stimulus to one or more electrodes.

In accordance with another aspect of the present invention, there is provided a wireless charging device operable for transmitting wireless energy to a receiving device. The wireless charging device includes an antenna for transmitting wireless energy over a wireless link to the receiving device during a power transfer cycle. A receiver coupled to the antenna of the charging device is operable to receive during the power transfer cycle one or more data messages from the receiving device. The charging device further includes a pulse loading detection circuit coupled to the antenna for detecting one or more pulse loading signals transmitted from the receiving device and outputting one or more corresponding pulse signals. A processor coupled to the pulse loading detection circuit detects each pulse width of the one or more pulse signals and differentiates between a pulse width of a first received pulse loading signal transmitted during a pulse loading communication session and a pulse width of a second pulse loading signal caused by switching regulation in the receiving device.

In another embodiment of the present invention, there is provided a method of transmitting a message from a wireless device to a wireless charging device. The method includes receiving wireless energy, via an antenna element, from the charging device. Switching regulation of the wireless energy is performed to generate a regulated voltage, and the switching regulation is disabled for a predetermined time period. The antenna element is pulse loaded during the predetermined time period thereby transmitting data to the charging device.

In accordance with yet another aspect of the present invention, there is provided a method of receiving a message at a wireless charging device from a wireless device. The method includes transmitting wireless energy over a wireless link to the receiving device during a power transfer cycle and receiving, during the power transfer cycle, one or more data messages from the wireless device. The receiving includes detecting one or more pulse loading signals transmitted from the wireless device and outputting one or more corresponding pulse signals, and detecting each pulse width of the one or more pulse signals and differentiating between a pulse width of a first received pulse loading signal transmitted during a pulse loading communication session and a pulse width of a second pulse loading signal caused by switching regulation.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 6A and 6B are examples of a message/coding table (FIG. 6A) and a protocol and bit timing diagram (FIG. 6B) that may be used in accordance with the present invention.

DETAILED DESCRIPTION OF THE INVENTION

The general principles of the present invention is described with respect to an implantable pulse generator (IPG) for generating electrical stimulation for application to a desired area of a body, such as a spinal cord stimulation (SCS) system. It will be understood that the present invention is not limited to an IPG for use in an SCS system, but has broad applicability, including but not limited to different types of implantable devices such as spinal and neural stimulators and sensors, deep brain stimulators, cochlear stimulators, drug delivery systems, muscle tissue stimulators, and the like, including sensors and sensing systems. The present invention is further applicable in systems powered by a replenishable power source wherein the power source is replenished using a recharging signal transmitted wirelessly from a charging device.

Figure 1:
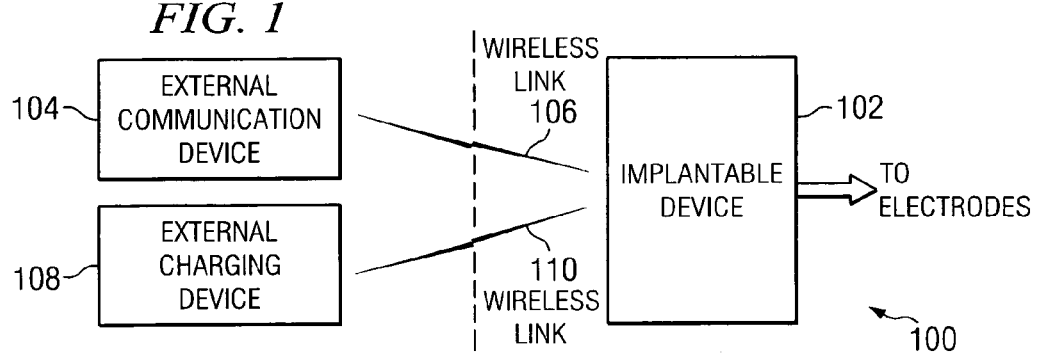
FIG. 1 is a block diagram of a stimulation system in accordance with the present invention.

Now referring to FIG. 1, there is shown a stimulation system 100 (generally, reference numeral 100) having an implantable pulse generator (IPG) 102, an external communication device 104 (sometimes referred to as an external programming device) and an external charging device 108. The external communication device 104 communicates with the IPG 102 via a wireless communications link 106 and provides functionality and control mechanism to program and control the operating characteristics of the IPG 102, and for other communications between the IPG 102 and device 104. The external charging device 108 transmits a charging signal that is received by IPG 102 via a wireless link 110 and is utilized to recharge a replenishable power source within the IPG 102. The IPG 102 provides electrical pulses or stimulation to a plurality of electrodes or electrode arrays (via a lead extension or lead body) for application at the desired location.

It will be understood by those skilled in the art that the external communications device 104 and the external charging device 108 may be combined into a single device.

Figure 2:
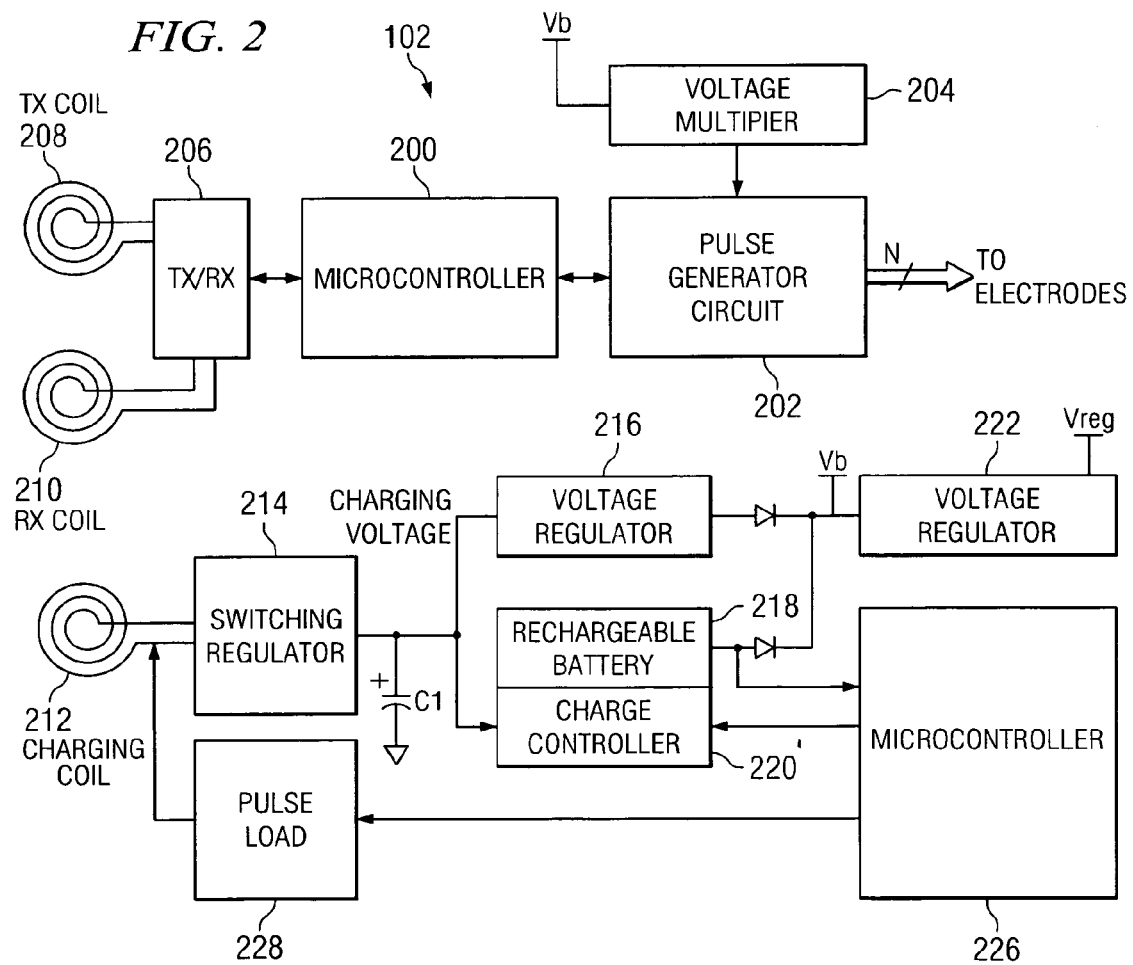
FIG. 2 is a detailed block diagram of the IPG shown in FIG. 1.

Now referring to FIG. 2, a microcontroller 200 and a pulse generator circuit 202 function to program, control and generate electrical signals (stimulation) output to a desired location (via the electrodes). The pulse generator circuit 202 generates a plurality electrical signals for output (i.e., "pulse generator outputs" or "outputs"). The microcontroller 200 generally includes a processor and memory (not specifically shown) and may further be constructed using any hardware, firmware and/or software, or combinations thereof, to provide the functionality described herein. A voltage multiplier 204 generates step-up and/or step-down voltages from a voltage supply Vb for supplying power to the pulse generator circuit 202. The microcontroller 200 and circuit 202 are shown as separate elements, but their functionality may also be provided by a single element (or multiple elements). Further, the pulse generator circuit 202 and microcontroller 200 may include various elements of hardware and/or software.

The microcontroller 200 receives/transmits data and other control signals from/to the external communications device 104 using a transceiver 206 and transmit and receive antenna elements 208, 210. The antenna elements 208, 210 may be one element or separate elements, and may further be constructed of various materials and configurations sufficient to provide the functionality of an antenna element to receive/transmit wireless signals. In one embodiment, the antenna elements are in the form of coils.

A switching regulator 214 receives energy contained with a charging signal received through a charging coil or antenna 212. The received energy is received inductively through the charging coil 212 from the external charging device 108 (FIG. 1) and utilized to recharge a replenishable power source 218 (e.g. rechargeable battery). The charging signal (from the external charging device), and in one embodiment is an RF signal of 2 Mhz, generates a corresponding signal within the charging coil 212. The received signal is rectified by a rectification circuit (not shown, and in one embodiment the rectification circuit includes a full wave bridge rectifier, series capacitor (for filtering) and an optional fuse for safety purposes) and output as an unregulated charging voltage supply. The output of the rectification circuit is input to the switching regulator 214 and coupled to a load pulsing circuit 228. The load pulsing circuit 228 provides a selectively switchable load for increasing the load on the charging coil 212, and is described in more detail further below.

The switching regulator 214 functions to generate a regulated charging voltage for input to the rechargeable battery 218 (to provide power for recharging) and a voltage regulator 216. A capacitor C1 is coupled to the output (regulated charging voltage) of the switching regulator 214 to hold up, or maintain its voltage level during short interruptions of the charging coupling occurring during a pulse loading communications window (as will he described more fully below). The voltage regulator 216 generates and outputs a regulated voltage which is coupled to a diode, as shown in FIG. 2. The rechargeable battery 218 is also coupled to a diode (as shown), and both diodes are coupled to a node for providing the voltage supply Vb which provides power (Vb) to other circuitry in the IPG 102. Such power configuration functions to allow the voltage source for the Vb node to be either the voltage supply from the linear regulator 216 or the rechargeable battery 218, whichever is greater. In normal operation, the voltage source for the Vb node will be the rechargeable battery 218, and during a charging session, it will be from the charging voltage (via the regulator 216). In other words, when sufficient energy is supplied by the switching regulator 214 (charging energy) to generate the regulated voltage higher than the battery voltage, this regulated voltage from the regulator 216 is used to supplant the battery voltage for powering downstream circuitry. A second voltage regulator 222 regulates the voltage Vb to generate another regulated voltage Vreg for use with circuitry requiring a lower voltage supply.

In one example embodiment, the unregulated charging voltage is about 12 volts or greater, while the regulated charging voltage output from the switching regulator 214 is about 6 volts. The output of the voltage regulator 216 is about 4.2 volts while the battery voltage is about 4 volts. With the voltage drop across the diodes, the node Vb will generally be between about 4 and 4.2 volts minus a diode voltage drop. The voltage supply Vreg can be on the order 3.3 to 2.5 volts, as desired.

The IPG 102 includes a microcontroller 226 that initiates and controls communication to the external charging device via a pulse loading communication technique in conjunction with the pulse loading circuit 228. The microcontroller further enables, disables and controls charging of the replenishable power source 218 via a charge controller 220, and monitors status of the charging operation (e.g. enable charger, charging signal present, charging current, charging voltage, etc.). As will be appreciated, the microcontroller 226 generally includes a processor and memory (not specifically shown) and may further be constructed using any hardware, firmware and/or software, or combinations thereof, to provide the functionality described herein. In another embodiment, the microcontroller 200 and the microcontroller 226 may be combined into a single microcontroller or processor.

The charge controller 220 is coupled to the replenishable power source 218 and the microcontroller 226 and is operable to control the charging of the replenishable power source 218. On one embodiment, charging occurs at a constant current until the replenishable power source 218 reaches a target voltage. Thereafter, the charging switches to constant voltage control while the current into the replenishable power source 218 decreases as it continues to charge.

The microcontroller 226 monitors the voltage of the replenishable power source 218 and charging voltages, and is further operable to detect various voltage levels (e.g., low battery, dead battery, etc.). When the voltage(s) reach certain levels, the IPG 102 (and/or other circuitry) is signaled and may go into various modes, such as a sleep mode when the voltage falls below a predetermined level. This voltage monitoring may also be accomplished using other element(s) (not shown) in addition to, or in lieu of, the microcontroller 226.

It is desirable to transmit error or status information (e.g., charging status and voltage, battery voltage levels, temperature overheat, overcurrent, and other operational parameters, etc.) during a recharging session from the IPG 102 to an external device. In prior art systems, such communication is accomplished using a wireless transceiver, similar to the transceiver 206 (FIG. 2) of the present invention, when communication is established with the external communications device 104. However, as mentioned above, the RF recharging energy present during a recharging session is substantial and may interfere with the other communications path between an implantable device and the external communications device. As such, the present invention provides a method and means for communication from the IPG 102 to the external charging device during a recharging session (or cycle). The present invention provides a pulse loading communications technique that minimizes corruption of data transmitted from the IPG 102. One embodiment of the present invention disables the switching regulation in the IPG 102 for a short period of time (to provide a pulse loading communications window) and further utilizes a communications protocol that reduces the likelihood that noise or switching regulation effects will be misinterpreted as transmitted data.

Figure 3:
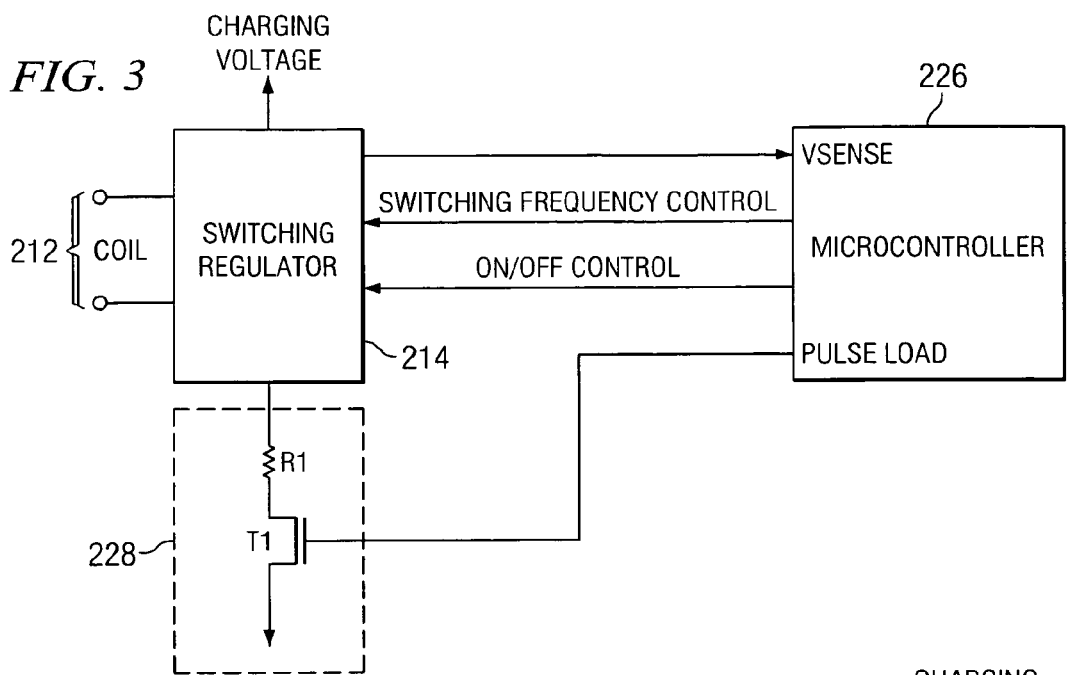
FIG. 3 illustrates one embodiment of the pulse loading circuitry.

Now referring to FIG. 3, there is shown the switching regulator 214, the microcontroller 226, and one embodiment of the pulse loading circuit 228. The switching regulator 214 operates at a switching frequency (Fswitch) during a recharging cycle. In one embodiment, circuitry (not shown) is provided that automatically changes the switching frequency to maintain the regulated voltage and an RC time constant circuit (or other circuit) operates to maintain the switching frequency below a particular frequency (as described in more detail herein). In another embodiment, the microcontroller 226 may increase or decrease the switching frequency (switching frequency control signal) depending on the value of the output voltage of the regulator 214 (VSENSE). In addition, an on/off control signal operates to enable/disable operation of the switching regulator 214. During a communications transmission period when pulse loading communications are operable, the switching regulator 214 is disabled.

The pulse loading circuit 228 is coupled to the charging coil to selectively increase the load on the charging coil 212. The pulse loading circuit 228 includes a resistive element R1 and a transistor switch T1, as shown. Other configurations and elements are possible. The pulse loading signal and the pulse loading circuit 228 are used to pulse load the charging coil 212.

Pulse loading effectively increases the current load on the coil 212 which is detectable at the external charging device 108, thus providing a mechanism to effectively communicate to the external charging device 108. Therefore, the coil 212 that is used to receive recharging energy is also used to send messages back to the charging device 108. In addition, because the energy "taken out" of the coil 212 during pulse loading is charging energy, and because the circuitry utilized in the IPG 102 to perform the load pulsing communications uses the charging energy and does not actively transmit energy (which would occur if the transceiver 206 were used), no energy from the replenishable power source 218 is used.

As will be appreciated, during the recharging cycle, the operation of the switching regulator 214 effectively pulse loads the coil 212. This occurs because the load on the charging coil 212 is increased/decreased according to the operation of the switching regulator 214. As such, each switching (on/off) of the switching regulator 214 is also detectable at the external charging device 108. To assist the external charging device 108 in recognizing the desired pulse loading, as opposed to pulse loading resulting from the switching regulation, the present invention (1) disables the switching regulator 214 during a predetermined time period during which the "true" data is transmitted, (2) operates the switching regulator 214 (during enabled operation) at a switching frequency Fswitch that is less than the data hit rate of the pulse loading communication, and (3) employs a communication and data message protocol to reduce the likelihood that noise or switching regulation will be interpreted as valid data.

Figure 4:
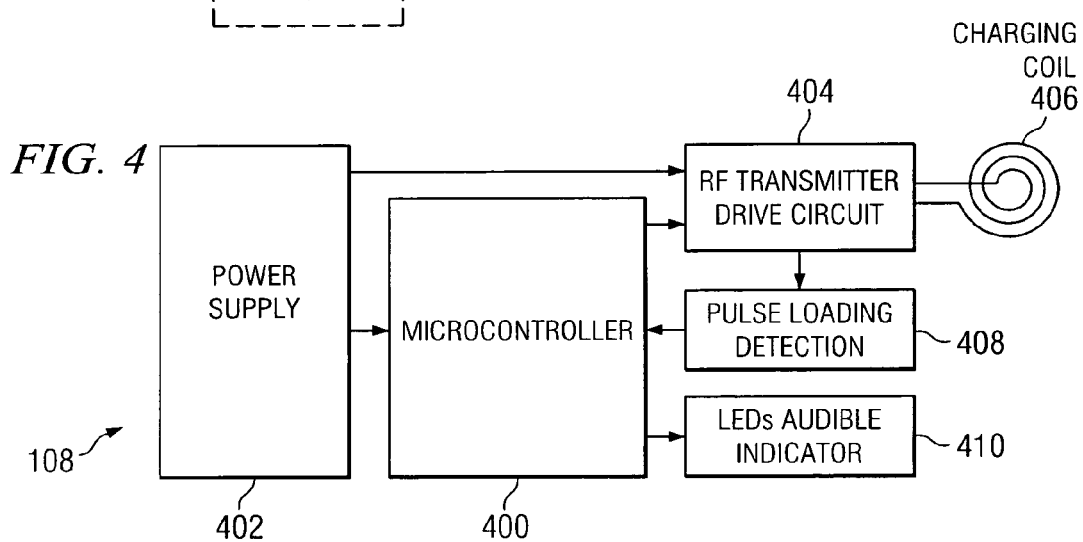
FIG. 4 is a detailed block diagram of the charging device shown in FIG. 1.

Now referring to FIG. 4, there is illustrated the charging device 108 in accordance with the present invention. The charging device 108 includes a microcontroller 400, a power supply 402, an RF transmitter drive circuit, a transmit coil or antenna 406, a pulse loading detector 408 and an output device 410.

The power supply 402 provides power to the various elements of the charging device 404 and may include one or more voltage regulators, and further may receive power from an external power supply (AC or DC). The microcontroller 400 functions to control the charging operation, monitor and detect data received by the charging device 108 via pulse loading, and control and output various indicators for recognition by a user. As will be appreciated, the microcontroller 400 generally includes a processor and memory (not specifically shown) and may further be constructed using any hardware, firmware and/or software, or combinations thereof, to provide the functionality described herein. The microcontroller further includes a digital signal processor (or other circuitry, firmware, and/or software) operable for detecting (or differentiating) pulse loading communications from pulse loading resulting from noise or switching regulation operation in the implantable device 102. One way of detecting or differentiating between the two pulse loading detections is to measure pulse widths and/or frequency of received signals. In one embodiment, the frequency of operation of the switching regulation is maintained at a frequency that is less than the frequency of the data bit rate utilized for the actual data communications. In another embodiment, or in addition to the above, a novel communication protocol may be used. Such a protocol is described more fully below.

The transmitter drive circuit 404 includes driver circuitry for transmitting a charging signal to the transmit coil 406 for transmission. Thus, the charging device 108 transmits RF energy to provide power to another device (e.g., to charge a battery). The transmitter drive circuit 404 may optionally include a current limiting device (not shown) to limit the current supplied to the circuit 404, and thus limit the amount of RF energy output.

The pulse loading detector 408 detects pulse loading, which occurs when a load that is receiving the RF energy transmitted by the charging device 108 is changed substantially (i.e., load switched in/out). The detector 408 may optionally include circuitry providing a filtering function to assist in properly detecting pulse loading.

The output device 410 provides visible and/or audible outputs controlled by the microcontroller 400 responsive to data received via the pulse loading. The output device 410 may include different color LEDs, audible indicators operable to provide different tones, and the like, or any other output mechanism to provide an indicator to a user.

The general operation of the system of the present invention will now be described. During a recharging cycle, the IPG 102 receives energy (transmitted from the charging device 108) at the charging coil 212. The received energy is converted to an unregulated voltage and input to a switching regulator (operating at a switching frequency Fswitch) to generate a regulated voltage. The regulated voltage thereafter provides power to operate some or all of the circuitry in the IPG 102 and charge the replenishable power source 218 (e.g. rechargeable battery).

In order for the IPG 102 to communicate information (such as battery, charging and status information, and any other desired information) to the external charging device 108 during the recharge cycle, the IPG 102 employs intentional pulse loading of the charging coil 212 to relay data bits back to the external charging device 108. Switching regulation occurring in the IPG 102 is disabled for a predetermined period of time (pulse loading communications window) to allow pulse loading communications to occur. Pulse loading communication is accomplished by selectively switching in and out a load on the charging coil 212 which corresponds to logic ones and zeros (data bits). The present invention provides that pulse loading (e.g., data bit rate) occurs at a frequency that is greater than the switching regulation frequency. Optionally, data is transmitted using a predetermined coding scheme to reduce the likelihood of errors during detection (or falsely detecting a data message during operation of the switching regulator or caused by other noise).

Pulse loading within the IPG 102 (i.e., the charging coil 212) generates corresponding and detectable signal(s) in the transmit coil 406 of the external charging device 108. Detected pulses are signal processed to detect/differentiate received "true" data from pulses resulting from switching regulation or noise. Upon detection and decoding of the data message(s), the external charging device 108 outputs corresponding indicia (such as LEDs, other display means, and/or audible signals) for communication to a user. As will be appreciated, the external charging device 108 may also perform other functions in response to the received data communication.

Figure 5:
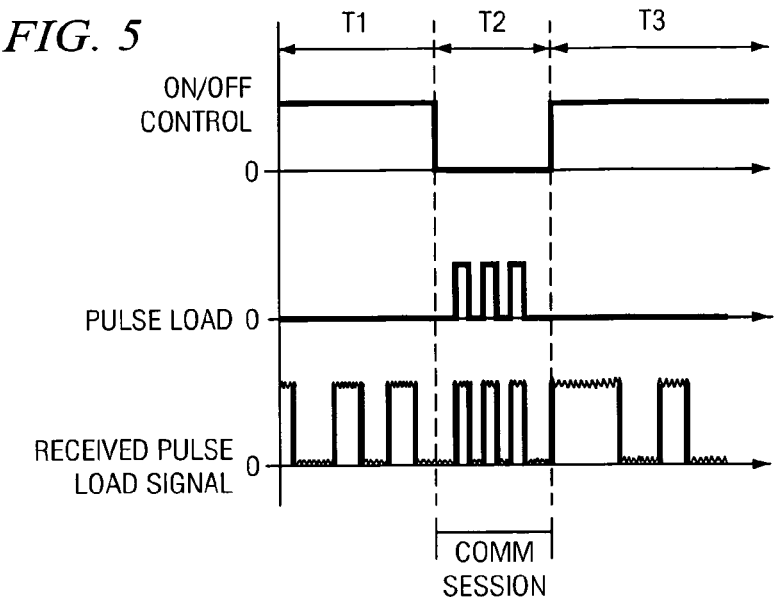
FIG. 5 is a diagram illustrating timing of the switching regulator control signal and pulse load signal generated by the IPG, and the pulse load signals received by the charging device.

Now referring to FIG. 5, there is shown a timing diagram illustrating aspects of the present invention. The timing diagram illustrates various events occurring during a recharging cycle, and more specifically identify (1) the switching regulator on/off control signal (to enable/disable operation), (2) pulse loading signal (output from the microcontroller 226 and controlling the pulse loading circuit 228), and (3) the signal output from the pulse load detector 408 in the external charging device 108.

During a time T1, the switching regulator 214 is active, data pulse loading is inactive, and the signal output from the pulse detector 408 shows pulses being detected (due to active switching regulation in the IPG 102, e.g., charging the battery), as shown. During time period T2 (pulse loading communication window), the switching regulator 214 is deactivated, data pulse loading becomes active, and the signal output from the pulse detector 408 shows that the data pulse loading is correspondingly detected, as shown. During time T3, the switching regulator 214 is again active, data pulse loading is inactive, and the signal output from the pulse detector 408 shows pulses being detected (due to the active switching regulation).

In one embodiment of the present invention, the switching regulator 214 is operated at a frequency Fswitch that is less than the data bit rate (or frequency) of the pulse loading data. As will be appreciated, the magnitude of the difference in these frequencies will depend on the signal processing capabilities and functionality of the external charging device

108. Moreover, it will be understood that different detection methods and means may be utilized to detect or differentiate the received data pulses from received pulses resulting from switching regulation or other noise ("unwanted" pulse loading detection). Using pulse width and/or frequency delineation is one method in accordance with the present invention.

To further reduce the likelihood of misinterpretation caused by switching regulation or other noise, a communications protocol, data coding and message scheme is provided. Typical data messages may include data for commands, status, state and errors. Now referring to FIGS. 6A and 6B, there is illustrated one embodiment of a message/coding table (FIG. 6A) and a protocol and bit timing diagram (FIG. 6B) in accordance with the present invention.

In one embodiment of the present invention, a data message includes a start sequence (or bits), code, and stop bit (or sequence). In the example, the start sequence includes a 00101 sequence of bits, the code includes four data bits (representing codes 0 to 15; EOLH and EOLL refer to the contents of high and low nibbles of an end-of-life (EOL) register in the IPG 102), and the stop bit includes a single logic zero data bit. The data bit width is shown as 122 microseconds, corresponding to a data bit rate or frequency of around 8 KHz or higher. Other data bit rates or frequencies may be used. In one embodiment of the present invention, the data bit rate (or frequency) is greater than switching frequency Fswitch of the switching regulator 214. As will be appreciated, other data message structures (start sequence, code, stop sequence, etc.) may also be utilized. As described, one embodiment of the start sequence is a 00101 start sequence that enhances the probability of proper decoding of messages or codes. Other sequences or bit(s) may be used.

Figure 6B:
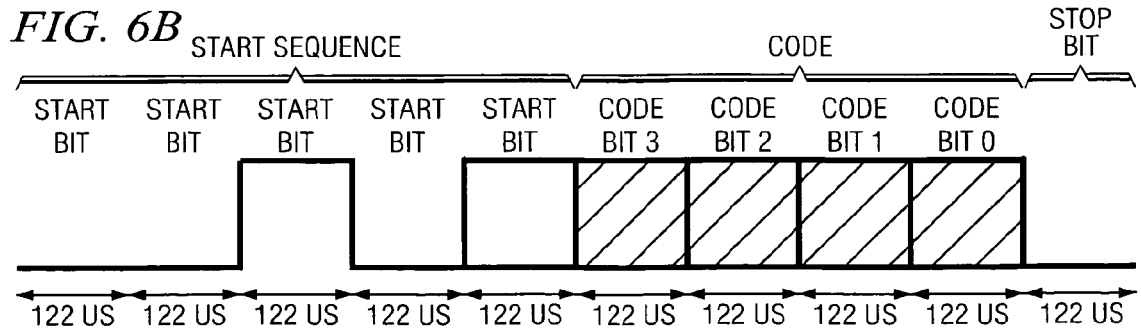

The table shown in FIG. 6A illustrates examples of codes and their associated messages. Other and different messages and coding techniques may be used, in addition to those shown. A corresponding message is determined based upon three codes (transmitted separately in data messages). For example, three separate data messages (as shown in FIG. 6B) each including a code are used to correspond or represent a given message. The external charging device 108 includes functionality to decode and interpret the separate data messages and messages/information corresponding thereto. The resulting information is then transmitted to the user by means of the output device 410. Such messages/information may relate to charging, faults, status, errors, and/or commands, or combinations thereof, and the like.

Accordingly, the general operation of transmitting a message pulse loading communication occurs as follows: The IPG 102 disables the switching regulator 214 to provide pulse communications window. A data message (similar to that shown in FIG. 6B, with a code) is transmitted using the pulse loading technique during the window, and the switching regulator is enabled. This operation is then repeated a second and third time, with a second code and third code respectively. The charging device 108 receives, detects, and decodes the data messages to determine the information transmitted. Based upon this, the charging device 108 outputs an indicator or indicators to a user notifying the user of the message or condition.

Other data bit timing, protocol and coding schemes are contemplated by the present invention. Such may be used to increase data integrity and correctly decode the transmitted message/information. Optionally, the data messages may he transmitted/received multiple times before a message is deemed valid for communication to the user.

It will be understood that the present invention is not limited to communications and operation only during a recharge cycle for an IPG, but may also be utilized during power transfer to (and operation of) an externally-powered IPG. Communications from the IPG 102 using a wireless power link that is providing power to the IPG 102 from an external device (104 or 108) are contemplated by the present invention. Moreover, the present invention is not limited to implantable devices (and "external" devices), but may also be practiced in other devices that receive power wirelessly (whether or not one device is implanted).

Figure 7:
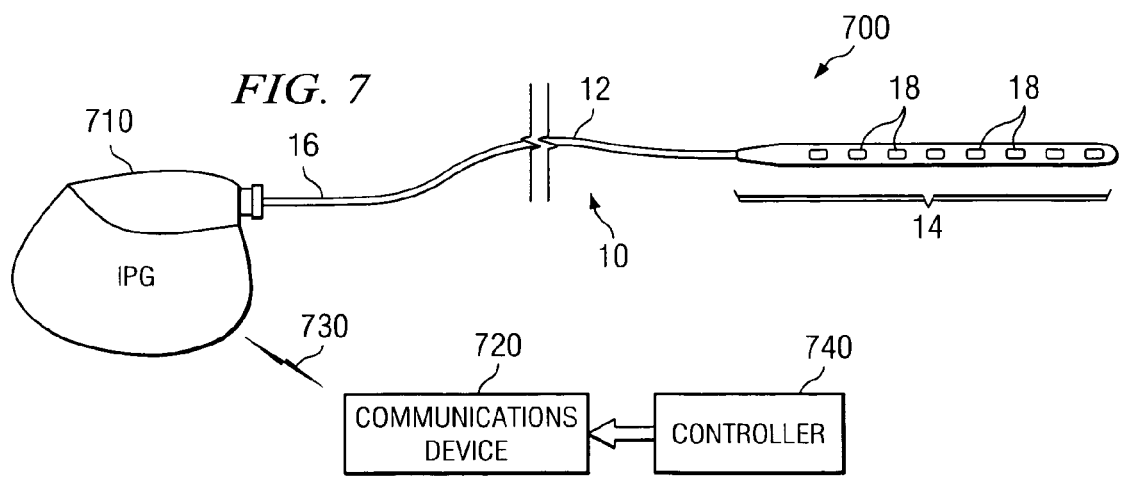
FIG. 7 illustrates a stimulation system in accordance with the present invention.

With reference to FIG. 7, there is shown a stimulation system 700 in accordance with the present invention. The stimulation system 700 generates and applies a stimulus to a tissue or to a certain location of a body. In general terms, the system 700 includes an IPG 710, in accordance with that described herein, that provides a stimulation or energy source and a lead 10 for application of the stimulus. The lead 10 shown in FIG. 7 is described below.

The lead 10 includes a distal end 14 and a proximal end 16. The lead 10 includes a lead body 12 that extends from the distal end 14 to the proximal end 16. The distal end 14 of the lead 10 is shown including four electrodes 18. The proximal end 16 of the lead 10 includes four contact electrodes (or ring electrodes) (not shown) that form a lead connector. The lead 10 generally includes one or more conductors (not shown) extending a substantial portion of the lead 10 to electrically connect the contact electrodes to respective electrodes 18. An optional lumen (not shown) may extend through the lead 10 and may be used for different purposes, including the delivery of chemicals or drugs.

As will be appreciated, any number of conductors and electrodes may be utilized, as desired. For purposes of illustration only, the lead 10 is shown with four electrodes. In addition, other types, configurations and shapes of electrodes (and lead connectors) as known to those skilled in the art may be used, as desired.

Typically, the lead body 12 is a structure having a round cross-section. Alternatively, the cross-section of the lead body 12 may be configured in any number of cross-sectional shapes appropriate for the specific application. The following description generally refers to a round cross-sectional shape for the lead body 12 for illustrative purposes only. The lead body 12 generally includes a lead body insulator configured to insulate the conductors and present a biocompatible external surface to the body tissue.

The lead body insulator is formed of insulating material typically selected based upon biocompatibility, biostability and durability for the particular application. The insulator material may be silicone, polyurethane, polyethylene, polyamide, polyvinylchloride, PTFT, EFTE, or other suitable materials known to those skilled in the art. Alloys or blends of these materials may also be formulated to control the relative flexibility, torqueability, and pushability of the lead. Depending on the particular application, the diameter of the lead body 12 may be any size, though a smaller size is more desirable for neurological and myocardial mapping/ablation leads and neuromodulation and stimulation leads.

The conductors (not shown) may take the form of solid wires, drawn-filled-tube (DFT), drawn-brazed-strand (DBS), stranded wires or cables, ribbon conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. The number, size, and composition of the conductors will depend on the particular application for the lead 10, as well as the number of electrodes.

The conductors may be configured along the lead body 12 in a straight orientation or spirally or helically wound about the optional lumen or center of the lead body 12. The conductors are typically insulated from the optional lumen, from each other, and from the external surface of the lead 10 by insulative material. The insulative material may be of a single composition, or multiple layers of the same or different materials.

In one embodiment, the lead 10 is generally configured to transmit one or more electrical signals from a source for application at, or proximate to, a spinal nerve or peripheral nerve, or other tissue.

The electrodes are typically made of a conductive material such as platinum, gold, silver, platinum-iridium, stainless steel, MS35N, or other conductive materials, metals or alloys known to those skilled in the art. The size of the electrodes is generally chosen based upon the desired application.

As shown in FIG. 7, the stimulation system 700 includes the lead 10 that is coupled to the IPG 710.

In one embodiment, the IPG 710 may include a self-contained implantable pulse generator (SCIPG) or externally-powered implantable pulse generator (EPIPG). As used herein, an SCIPG is an IPG having an implanted power source, such as a long-lasting or replenishable power source (e.g. rechargeable battery). An EPIPG is an IPG that does not include a long-lasting or replenishable power source and that receives its operating power from an external power transmitter, preferably in the form of a wireless signal (RF, inductive, etc.). As is known in the art, an IPG is capable of being implanted within the body (not shown) that receives electrical stimulation from the IPG 710.

An external communications device 720 (the same as or similar to the device 104, or programmer/controller) may be provided to control and/or program the IPG 710 via a communications link 730 (same as or similar to the communications link 106). When in the form of an SCIPG with a replenishable power source, the device 720 may also provide power to the IPG 710 through an integrated or separate charging device (the same as or similar to charging device 108). When in the form of an EPIPG, the device 720 usually provides both power and control communications to the IPG 710. A separate controller 740 may be provided which controls/programs the device 720. In some embodiments, the controller 740, or collectively the device 720 and controller 740, are referred to as an external patient controller/programmer (EPP).

As shown in FIG. 7, the stimulation system 700 includes the lead 10 that is coupled to the IPG 710. The IPG 710 is the same as or similar to the IPG 102. Communication/power signals are represented in FIG. 7 by the wireless link symbol 730 (the same as or similar to links 106 and 110 in FIG. 1). The device 720 and the controller 740 are located external to the body that is to receive electrical stimulation from the IPG 710. A user of the IPG 710 may use the device 720 and/or controller 740 to provide control signals for the operation of the IPG 710. The controller 740 provides control signals to the device 720. The device 720 transmits the control signals (and optionally power) to a receiver in the IPG 710, and the IPG 710 responds to the control signals to vary the signal parameters of the electrical signals that are transmitted through lead to the stimulation site.

As will be appreciated, the contact electrodes are not visible in FIG. 7 because the contact electrodes are situated within a receptacle (not shown) of the IPG 710. The contact electrodes electrically connect to a pulse generator circuit within the IPG 710. The IPG 710 generates and sends electrical signals via the lead 10 to the electrodes 18. Understandably, the electrodes 18 are located at a stimulation site (not shown) within the body that is to receive electrical stimulation from the electrical signals. A stimulation site may be, for example, adjacent to one or more nerves in the central nervous system (e.g., spinal cord). The IPG 710 is capable of controlling the electrical signals by varying signal parameters (e.g., intensity, duration, frequency) in response to control signals that are provided to the IPG 710.

It may be advantageous to set forth definitions of certain words and phrases that may be used within this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, such a device may be implemented in hardware, firmware or software, or some combination of at least two of the same. It should be noted that the functionality associated with any particular controller may be centralized or distributed, whether locally or remotely. The term "couple" or "connect" refers to any direct or indirect connection between two or more components, unless specifically noted that a direct coupling or direct connection is present.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for receiving wireless energy from a charging device, the device comprising:
    an antenna element operable for receiving wireless energy transmitted from the charging device;
    a switching regulator coupled to the antenna element and having circuitry for enabling operation of the switching regulator during a first predetermined time period and for disabling operation of the switching regulator during a second predetermined time period in response to a switching regulator control signal, the switching regulator operable for receiving and regulating the received wireless energy and outputting a regulated voltage; and a pulse loading circuit coupled to the antenna element and operable for receiving one or more pulse loading pulses during the second predetermined time period and pulse loading the antenna element in response to the one or more pulse loading pulses, and wherein the pulse loading the antenna element is operable to transmit data to the charging device.

2. The device in accordance with claim 1 wherein the device comprises an implantable device configured for implantation within a body, and the charging device is operable for use externally to the body and provide a source of wireless energy.

3. The device in accordance with claim 1 wherein the switching regulator operates at a first switching frequency and the data transmitted to the external device has a data bit rate of a second frequency higher than the first switching frequency.

4. The device in accordance with claim 1 wherein operation of the switching regulator affects the antenna element sufficient to generate signals detectable in the charging device.

5. The device in accordance with claim 1 wherein the pulse loading circuit further comprises:
    a switch coupled to the antenna element; and
    a resistive element connected to the switch and to a first voltage supply for diverting a current from the antenna element.

6. The device in accordance with claim 1 further comprising a circuit for generating the switch regulator control signal and the one or more pulse loading signals thereby initiating pulse loading communication between the device and the charging device.

7. The device in accordance with claim 1 further comprising a replenishable power source coupled to the regulated voltage signal, the regulated voltage operable for replenishing the replenishable power source, and wherein the pulse loading occurs during a recharge cycle of the device.

8. The device in accordance with claim 1 wherein the charging device provides power to the device for at least a one of: operating the device and replenishing a replenishable power source within the device.

9. The device in accordance with claim 1 further comprising a circuit for monitoring a recharging session during which a replenishable power source within the device is recharged using wireless energy transmitted from the charging device, and wherein the pulse loading the antenna element is operable to transmit information relating to recharging of the replenishable device to the charging device during the recharging session.

10. A wireless charging device operable for transmitting wireless energy to a receiving device, the wireless charging device comprising:
    an antenna for transmitting wireless energy over a wireless link to the receiving device during a power transfer cycle; and
    a receiver coupled to the antenna for receiving during the power transfer cycle one or more data messages from the receiving device, the receiver further comprising:
        a pulse loading detection circuit coupled to the antenna for detecting one or more pulse loading signals transmitted from the receiving device and for outputting one or more corresponding pulse signals, and
        a processor coupled to the pulse loading detection circuit for detecting each pulse width of the one or more pulse signals and differentiating between a pulse width of a first received pulse loading signal transmitted during a pulse loading communication session and a pulse width of a second pulse loading signal caused by switching regulation in the receiving device.

11. The charging device in accordance with claim 10 further comprising:
    an output device coupled to the processor for outputting an indication to a user.

12. The charging device in accordance with claim 11 wherein the output device comprises at least one of the following: an LED and an audible indicator.

13. The charging device in accordance with claim 11 wherein a data message is received during the pulse loading communication, and said data message includes information relating to recharging of the receiving device.

14. A method of transmitting a message from a wireless device to a wireless charging device, the method comprising:
    receiving, via an antenna element, wireless energy from the charging device;
    performing switching regulation of the wireless energy to generate a regulated voltage;
    disabling the switching regulation for a predetermined time period; and
    pulse loading the antenna element during the predetermined time period thereby transmitting data to the charging device.

15. The method in accordance with claim 14 further comprising:
    performing the switching regulation at a first switching frequency; and
    transmitting data to the charging device at a data bit rate frequency that is higher than the first switching frequency.

16. The device in accordance with claim 14 wherein the switching regulation affects the antenna element sufficient to generate signals detectable in the charging device.

17. The device in accordance with claim 14 wherein the pulse loading further comprises diverting a current from the antenna element.

18. A method of receiving a message at a wireless charging device from a wireless device, the method comprising:
    transmitting wireless energy over a wireless link to the receiving device during a power transfer cycle; and
    receiving during the power transfer cycle one or more data messages from the wireless device, the receiving comprising,
        detecting one or more pulse loading signals transmitted from the wireless device and outputting one or more corresponding pulse signals, and
        detecting each pulse width of the one or more pulse signals and differentiating between a pulse width of a first received pulse loading signal transmitted during a pulse loading communication session and a pulse width of a second pulse loading signal caused by switching regulation.

19. A system for stimulating a portion of a body, the system comprising:
an implantable device for receiving wireless energy from a charging device and for generating a stimulus, the implantable device comprising,
an antenna element operable for receiving wireless energy transmitted from the charging device,
a switching regulator coupled to the antenna element and having circuitry for enabling operation of the switching regulator during a first predetermined time period and for disabling operation of the switching regulator during a second predetermined time period in response to a switching regulator control signal, the switching regulator operable for receiving and regulating the received wireless energy and outputting a regulated voltage, and
a pulse loading circuit coupled to the antenna element and operable for receiving one or more pulse loading pulses during the second predetermined time period and pulse loading the antenna element in response to the one or more pulse loading pulses, and wherein the pulse loading the antenna element is operable to transmit data to the charging device; and
an implantable lead for receiving the stimulus from the implantable device and applying the stimulus to one or more electrodes.

20. The system in accordance with claim 19 further comprising:
a controller operable for communicating with the implantable device and controlling the implantable device.

21. The system in accordance with claim 20 wherein the implantable device comprises an RF receiver.

* * * * *